(12) United States Patent
Bokelman et al.

(10) Patent No.: US 6,198,537 B1
(45) Date of Patent: Mar. 6, 2001

(54) OPTICAL INSPECTION SYSTEM FOR THE MANUFACTURE OF BANDED CIGARETTE PAPER

(75) Inventors: Gordon H. Bokelman; Thomas A. Fletcher, both of Chesterfield; D. Anh Phan, Richmond; Yeu-Hwa Shyy, Fairfax; Ernest S. Houck, Alexandria, all of VA (US)

(73) Assignee: Philip Morris Incorporated, New York, NY (US)

( * ) Notice: Subject to any disclaimer, the term of this patent is extended or adjusted under 35 U.S.C. 154(b) by 0 days.

(21) Appl. No.: 08/893,538

(22) Filed: Jul. 11, 1997

(51) Int. Cl.[7] .................................................. G01N 21/84
(52) U.S. Cl. .............................................. 356/429; 131/905
(58) Field of Search .................................... 356/429, 430, 356/431; 131/907, 908, 905; 348/88

(56) References Cited

U.S. PATENT DOCUMENTS

| | | |
|---|---|---|
| 3,089,497 | 5/1963 | Molins et al. . |
| 3,588,513 | 6/1971 | Akamatsu et al. . |
| 3,818,223 | 6/1974 | Gibson et al. . |
| 3,955,584 | 5/1976 | Molins et al. . |
| 4,001,579 | 1/1977 | Lebet et al. . |
| 4,011,950 | 3/1977 | McLoughlin et al. . |
| 4,054,377 | 10/1977 | Gibson . |
| 4,090,794 | 5/1978 | Benini . |
| 4,099,884 | 7/1978 | Nash . |
| 4,212,541 | 7/1980 | Ducommun et al. . |
| 4,238,994 | 12/1980 | Koch . |
| 4,266,674 | 5/1981 | Bell et al. . |
| 4,377,743 | 3/1983 | Bolt et al. . |
| 4,398,546 | 8/1983 | Fisher et al. . |
| 4,423,742 | 1/1984 | Reuland . |
| 4,645,921 | 2/1987 | Heitmann et al. . |
| 4,671,663 | 6/1987 | Sick . |
| 4,682,038 | 7/1987 | Focke . |
| 4,718,026 | 1/1988 | Long et al. . |
| 4,756,317 | 7/1988 | Edwards . |
| 4,766,315 | 8/1988 | Hellstrom et al. . |
| 4,767,924 | 8/1988 | Giebel et al. . |
| 4,776,351 | 10/1988 | Wahle et al. . |
| 4,805,641 | 2/1989 | Radzio et al. . |
| 4,841,763 | 6/1989 | Kang et al. . |
| 4,845,374 | 7/1989 | White et al. . |
| 4,860,772 | 8/1989 | Hensgen et al. . |
| 4,865,054 | 9/1989 | Lorenzen et al. . |
| 4,875,494 | 10/1989 | Siems . |

(List continued on next page.)

OTHER PUBLICATIONS

"More Feedback: Process Control Leaps Ahead With New ABB Solutions [For Tobacco Manufacturing]", Tobacco Reporter (Nov. 1994) vol. 121, No. 11, P. 26, Doolittle, David E.

Primary Examiner—Richard A. Rosenberger
(74) Attorney, Agent, or Firm—Burns, Doane, Swecker & Mathis, LLP

(57) ABSTRACT

A station optically inspects banded cigarette paper by directing an elongated beam of white light laterally across a web of the cigarette paper. The elongated beam impinges on the surface of the cigarette paper and forms reflections. A plurality of line scan camera containing linear CCD arrays receive the reflections and generate output signals. One or more processing units process the output signals to generate data indicative of the spacing between bands, the width of the bands, and the contrast of the bands. These calculations can be periodically transferred to a separate computer workstation over a network. The workstation generates statistical reports on the basis of the calculations, such as the band width, band spacing and band contrast as a function of lane number, and as a function of time. The statistical reports provide a convenient way of quickly detecting irregularities in application of the bands. According to exemplary embodiments, the inspection station is designed for installation in a cigarette paper manufacturing system.

22 Claims, 12 Drawing Sheets

U.S. PATENT DOCUMENTS

| | | |
|---|---|---|
| 4,879,000 | 11/1989 | Gausa . |
| 4,906,099 | 3/1990 | Casasent . |
| 4,907,607 | 3/1990 | Focke et al. . |
| 4,915,827 | 4/1990 | Rosenthal . |
| 4,926,886 | 5/1990 | Lorenzen et al. . |
| 4,941,482 | 7/1990 | Heitmann et al. . |
| 4,963,743 | 10/1990 | Satake et al. . |
| 4,976,544 | 12/1990 | Neri . |
| 4,982,104 | 1/1991 | Yuito . |
| 4,986,285 | 1/1991 | Radzio et al. . |
| 5,000,323 | 3/1991 | Cahill et al. . |
| 5,006,722 | 4/1991 | Adelson . |
| 5,010,904 | 4/1991 | Lassiter . |
| 5,013,905 | 5/1991 | Neri . |
| 5,024,333 | 6/1991 | Brink et al. . |
| 5,061,063 | 10/1991 | Casasent . |
| 5,072,128 | 12/1991 | Hayano et al. . |
| 5,086,279 | 2/1992 | Wochnowski et al. . |
| 5,118,195 * | 6/1992 | Dobbie ................................. 356/430 |
| 5,150,175 * | 9/1992 | Whitman et al. .................... 356/429 |
| 5,166,748 | 11/1992 | Dahlquist . |
| 5,189,708 | 2/1993 | Cox et al. . |
| 5,208,870 | 5/1993 | Ennis . |
| 5,223,915 | 6/1993 | Neri . |
| 5,228,462 | 7/1993 | Osmalov et al. . |
| 5,235,649 | 8/1993 | Reda . |
| 5,237,621 | 8/1993 | Cox et al. . |
| 5,243,408 | 9/1993 | Whitman, III . |
| 5,305,392 | 4/1994 | Longest, Jr. et al. . |
| 5,341,824 | 8/1994 | Fletcher et al. . |
| 5,345,955 | 9/1994 | Clearman et al. . |
| 5,353,357 | 10/1994 | Longest, Jr. et al. . |
| 5,365,596 | 11/1994 | Dante et al. . |
| 5,366,096 | 11/1994 | Miller . |
| 5,406,376 | 4/1995 | Maiwaid et al. . |
| 5,410,396 | 4/1995 | Rochester . |
| 5,414,270 | 5/1995 | Henderson et al. . |
| 5,426,509 | 6/1995 | Peplinski . |
| 5,432,600 | 7/1995 | Grollimund et al. . |
| 5,448,365 | 9/1995 | Grollimund et al. . |
| 5,534,114 | 7/1996 | Cutright et al. . |
| 5,641,971 | 6/1997 | Prigent . |
| 5,718,249 | 2/1998 | Suzuki et al. . |
| 5,746,225 | 5/1998 | Okumoto et al. . |
| 5,762,075 | 6/1998 | Hoppe et al. . |
| 5,847,753 * | 6/1992 | Gabello et al. ........................ 348/88 |

\* cited by examiner

OPTICAL INSPECTION SYSTEM FOR THE MANUFACTURE OF BANDED CIGARETTE PAPER

CROSS-REFERENCE TO RELATED APPLICATIONS

The present application is related to commonly assigned Ser. No. 08/893,500 (our reference 021238-177/PM-1803) entitled "Bobbin Optical Inspection System" and Ser. No. 08/893,505 (our reference 021238-178/PM-1804) entitled "Cigarette Making Machine Including Inspection of Paper Containing Bands", both of which were filed on the same date as the present application. Both of these applications are incorporated by reference in their entirety herein.

BACKGROUND

The present invention relates generally to an optical inspection system for determining the characteristics of a moving web. More specifically, the present invention relates to an optical inspection system for determining the characteristics of a moving web of cigarette paper containing bands.

Commonly assigned U.S. Pat. Nos. 5,417,228 and 5,474,095 disclose cigarette papers comprising a base web and banded regions of add-on material. As illustrated in FIG. 1, an exemplary cigarette 7 might contain two bands 5 of material formed by depositing a layer of cellulosic pulp on base cigarette paper 3. Cellulon, microcrystalline cellulose, flax or wood pulp, or amylopectin are some of the various preferred substances which have been used to form the bands.

Commonly assigned U.S. Pat. No. 5,534,114 discloses that the above described bands can be formed by modifying a conventional Fourdrinier paper making machine to deposit additional layers of cellulose at some stage in the production of the cigarette base paper 3. To streamline process, the bands are preferably applied while the paper is moving at high speeds, such as 500 feet per minute. At these high speeds, breakdowns and other factors (such as clogged band applicators), can result in the production of a base web having misplaced bands.

For example, as illustrated in FIG. 2, common anomalies arise when the width of a band 1 deviates from a desired width 12, or the band becomes skewed so that it is no longer orthogonal with respect to the edge of the paper (as is the case with band 1). Other anomalies arise when the separation 2 between two bands deviates from a desired separation width 10 (also called "band spacing" herein). Moreover, an irregular band applicator may produce a band with gaps or a band having a contrast which is either too high (e.g. as in band 9) or too low.

The prior art includes web inspection devices for use in the manufacture of fabrics, film, paper and like material. Some of these devices include a light source for projecting electromagnetic radiation on a moving web of material. The light impinges on the surface of the moving web, where it is reflected and received at a detector device. Any anomalies in the moving web can be detected by investigating the nature of the reflected electromagnetic radiation. For instance, a tear, pinhole or blemish in the web will manifest itself in a spike in the signal level from the detector (which is attributed to an increase or decrease in reflected radiation). This spike can be viewed by connecting the detector output to an oscilloscope, as exemplified by U.S. Pat. No. 5,426,509 to Peplinkski.

While useful, these devices are ill-suited to the task of detecting the integrity of bands on cigarette paper. Bands formed on cigarette paper often have reflective properties similar to the cigarette paper itself. Often, for instance, the bands are formed of white colored material which is difficult to distinguish from the white colored cigarette paper. Moreover, the basis weight of the cigarette paper may vary along the direction of travel of the paper on the paper making machine (due to the difficulty in maintaining a constant pulp application rate). The variance in basis weight of the paper influences its reflective properties, thereby obfuscating the differences between banded and non-banded regions, which are subtle enough to begin with. The prior art devices do not have the ability to interpret a reflection from a web of this nature. As mentioned, these devices are configured to examine a web surface for tears, pinholes and blemishes which manifest themselves in dramatic spikes in the video camera signal.

Also, whether a band width is too long, too short, or separated from its neighboring band by more or less than a desired distance can not be determined by simply observing the properties of a single point on a moving web. Rather, the properties of a band should be gauged by determining the spatial relationship between different elements on the web.

Pattern recognition techniques are one way of determining the spatial relationship between different features on a printed web of material. In a common technique, a camera forms a digital image of a portion of a web of material and information printed thereon. The digital image is then compared with a pre-stored template representing an error-free web portion. Discrepancies between the template and the image represent an irregular web. These techniques offer accuracy, but unfortunately entail a great deal of data processing. These techniques are therefore ill-suited to detecting the properties of bands on a web which may be moving at speeds of greater than or equal to 500 feet per minute.

Accordingly, it is an exemplary objective of the present invention to provide an inspection system for accurately detecting the properties of bands contained on a moving web of cigarette paper without delaying other stages in the manufacture of the cigarette paper.

SUMMARY

These and other exemplary objectives are achieved according to the present invention through an inspection station which is mounted over a moving web in a paper making machine, downstream of a band applicator.

The paper inspection machine includes a mounting frame including a plurality of light sources. The light sources channel light via a fiber optic cable to a light distribution assembly. The light distribution assembly directs a narrow stripe of light across the web. The stripe of light is reflected at the paper surface and then received by a plurality of cameras, each containing a linear CCD array.

The data from the CCD arrays is fed to one of two processor units also mounted on the frame. The processing units divide the data from each array into a plurality of lanes. A single pixel from each lane is then compared with a dynamic threshold to determine whether the lane corresponds to a band region or a non-band region. By monitoring and recording the pixels from successive lanes, the processing units are able to compute the width of bands on the web, the spacing between bands, and the average contrast of the bands.

At periodic intervals, the information calculated by the units is assembled into an Ethernet packet and transferred over an Ethernet network to a computer workstation. The computer workstation then aggregates the packet with previously received packets and presents various summary statistical displays for the operator. For instance, the display provides graphs illustrating the band width, band spacing, band contrast, and band anomalies as a function of lane number for the most recent interval. Furthermore, the display presents cumulative statistics by presenting a graph of the band width, band spacing and band contrast as a function of time.

Among other advantages, the apparatus accurately assesses major cigarette band paper anomalies, and timely presents the information in a format which can be easily understood at a glance. For instance, the user can be apprised that a particular element in the band applicator is clogged by noting that a particular lane number is producing irregular bands. Further, the user can be apprised of a general trend of degradation in the system by observing the composite graphs discussed above, and thereby take prompt remedial action.

According to another particularly advantageous feature, the threshold used to discriminate band regions from non-band regions is dynamically set on the basis of moving averages of immediately preceding band regions and non-band regions. In one embodiment, the threshold represents the moving average of non-band background plus the greater of: (1) a set constant value (such as 10 gray levels) or (2) 50% of the moving average of banded region peak heights (where the "peak heights" correspond to the gray level of the banded region minus the gray level of a neighboring non-banded region). Dynamically setting the threshold in this manner accommodates a wide variety of different types of cigarette paper and band material, and also can account for changes in the basis weight (and other properties, such as chemical composition, opacity, etc.) of the paper along the direction of travel of the paper making machine.

BRIEF DESCRIPTION OF THE DRAWINGS

The foregoing, and other, objects, features and advantages of the present invention will be more readily understood upon reading the following detailed description in conjunction with the drawings in which.

DETAILED DESCRIPTION

In the following description, for purposes of explanation and not limitation, specific details are set forth in order to provide a thorough understanding of the invention. However it will be apparent to one skilled in the art that the present invention can be practiced in other embodiments that depart from these specific details. In other instances, detailed descriptions of well-known methods, devices, and circuits are omitted so as not to obscure the description of the present invention with unnecessary detail. In the Figures, like numbers designate like parts.

According to exemplary aspects, the inspection system of the present invention is designed to inspect the characteristics of cigarette paper during its manufacture. Thus, before discussing the inspection station itself, it is useful to first describe exemplary aspects of a cigarette paper manufacturing system.

Figure 1:
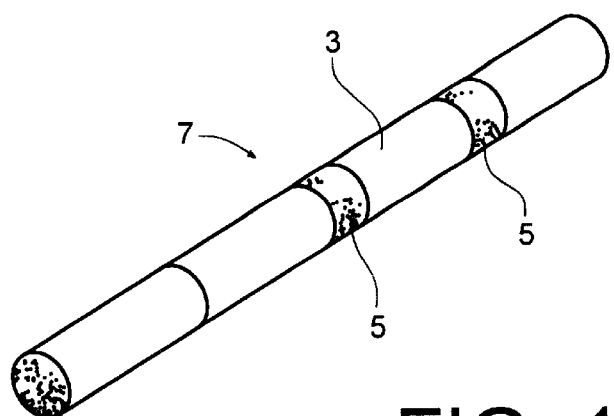
FIG. 1 shows an exemplary cigarette containing banded regions.
Figure 2:
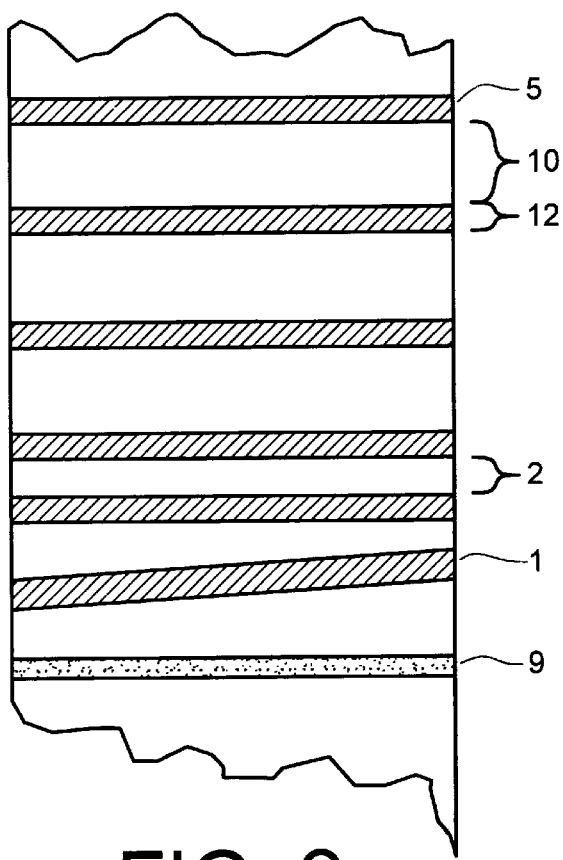
FIG. 2 shows an exemplary web of cigarette material including bands, some of which are irregular.
Figure 3:
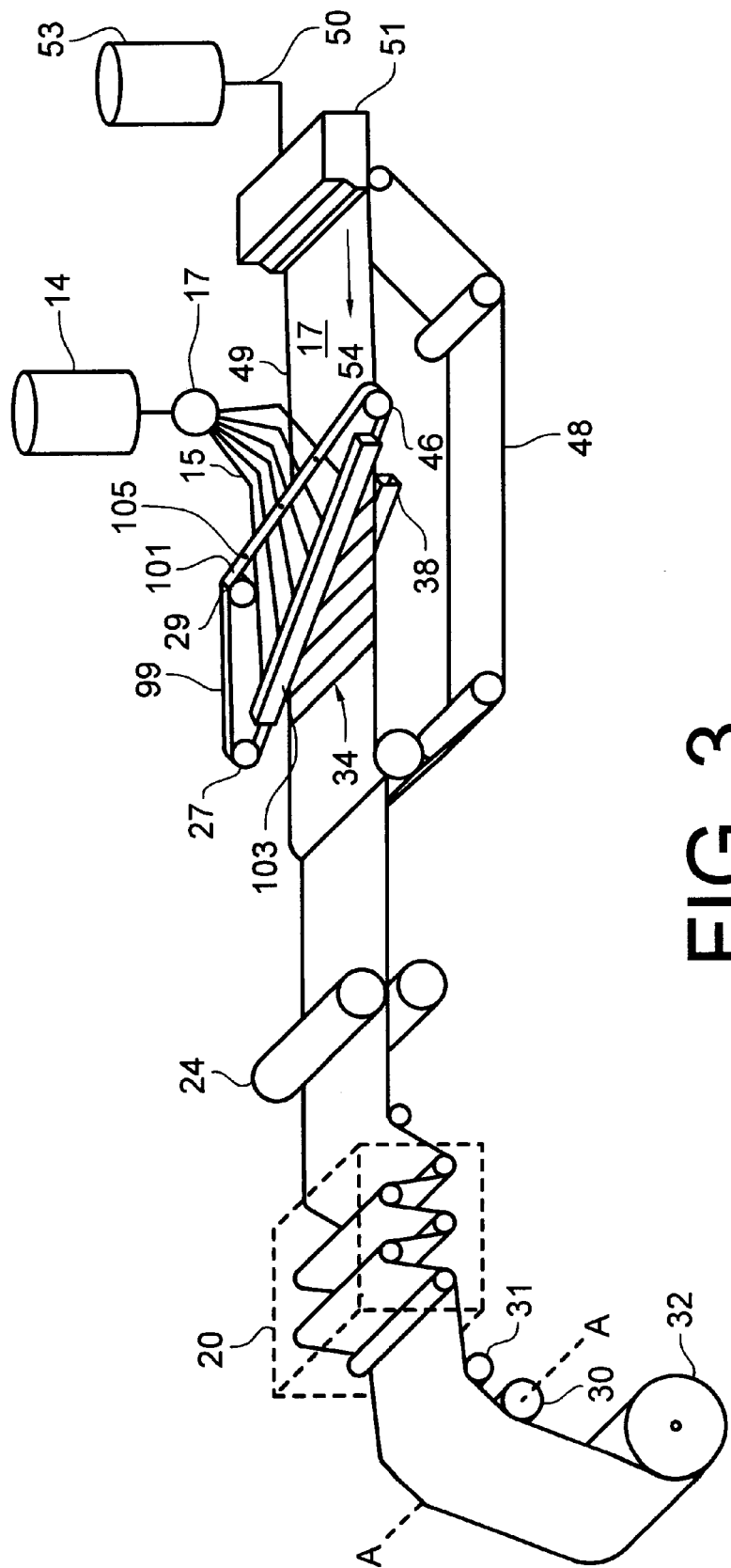
FIG. 3 shows an exemplary paper making machine in which the inspection station of the present invention can be employed.

FIG. 3 illustrates an exemplary machine for producing a web 17 of fibrous material. As shown there, a central tank 53 of refined pulp (such as refined flax or wood pulp) is delivered to a head box 51 by means of a plurality of conduits 50. The Fourdrinier wire 49 transports the slurry pulp from the head box 51 in the direction of the arrow 54. At this point, the pulp has a high moisture content. Water is allowed to drain from the slurry, and is also removed by vacuums (not shown). Reference numeral 48 shows the return loop of the Fourdrinier wire 49.

The band application assembly 99 is located downstream of the vacuums. Assembly 99 generally includes a frame housing an endless perforated steel belt (not shown), which is guided by drive wheel 27, guide wheel 29, and follower wheel 46. The bottom of the assembly 99 includes a chamber box (not shown) containing a reservoir of slurry supplied from day tank 14 via conduits 15. The flow of slurry through conduits 15 is maintained at appropriate levels by a flow distribution system comprising a series of pumps (not shown) in conjunction with a pressure monitoring system (not shown).

Slurry is dispensed through the perforations in the endless steel belt (not shown) as it passes through the bottom portion of the chamber box. The belt is moving as the slurry is dispensed, thereby compensating for the motion of the web moving beneath the chamber box. According to exemplary embodiments, the belt is moved at a rate of 1000 feet per minute to compensate for a Fourdrinier wire moving at a rate of 500 feet per minute. As a result of this compensation, the chamber box applies the bands (e.g. bands 34) so that they are orthogonal to the edges of the web 17. If the bands are not completely orthogonal, the angle of the band application assembly 99 can be adjusted. Alternatively, a non-orthogonal application of bands may be desired. Those interested in further details regarding the band application assembly 99 are referred to commonly assigned U.S. Pat. No. 5,534,114, the entire disclosure of which is incorporated herein by reference.

The banded paper then passes through one or more press rollers 24 which squeeze as much water out of the paper as possible through mechanical pressure. The remaining water can then be evaporated out of the paper by passing the paper over the surface of one or more drying rollers 20. These moisture removal techniques are conventional in the art and thus will not be discussed in further detail. Furthermore, those skilled in the art will appreciate that other moisture-removal techniques can be used to replace or supplement the above-identified techniques, such as the conventional use of a felt web to remove moisture from the paper.

According to exemplary aspects of the present invention, the inspection station of the present invention is positioned downstream from the drying rolls 20, just before the paper is wound on the final paper reel 32. More specifically, in the exemplary embodiment shown in FIG. 3, the inspection station is positioned over the roller 30, which follows roller 31, at a position denoted by the line A—A. Roller 30 can be a stationary stainless steel tube having a diameter of six inches. Those having skill in the art will recognize that the inspection station can be placed at a variety of locations downstream of the band application assembly 99, or more than one inspection station can be employed to inspect the paper web.

Figure 4:
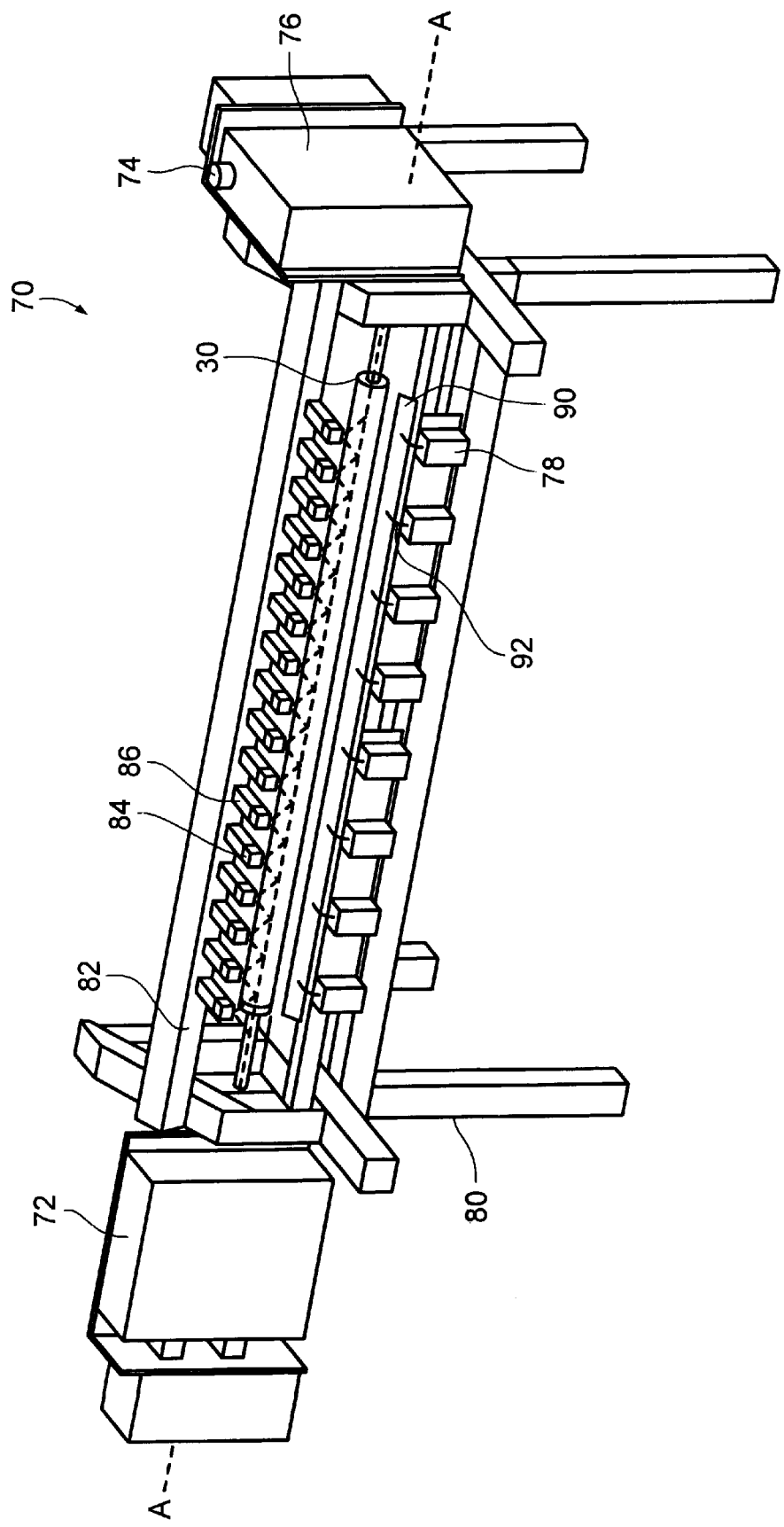
FIG. 4 shows an exemplary paper inspection machine of the present invention.

An exemplary inspection station 70 for use in connection with the paper making machine of FIG. 3 is shown in FIG. 4. By way of overview, the inspection station includes a frame 80 which straddles the Fourdrinier wire 49 over the roller 30. The inspection station 70 includes eight light sources, one of which is denoted by 78. The light sources are connected by fiberoptic cabling 92 to a light distribution assembly 90, which spans the lateral width of the roller 30. The light distribution assembly 90 directs the light onto the paper in a narrow line as the paper passes over the roller 30. Light is specularly reflected off the paper and received by one or more of sixteen cameras which span the length of the web, one of which is denoted by 84. Each camera can be individually positioned by means of adjustment mechanism 86, which adjustably fixes the cameras (e.g. 84) to an overhead bar 82 of the frame 80. Information from the cameras is transferred via electrical lines (not shown) to processing circuitry located in enclosures 72 and 76. More specifically, enclosure 72 includes processing circuitry which services the left-most four light sources and left-most eight cameras. Enclosure 76 contains processing circuitry which services the remaining right-most four light sources and eight cameras. According to exemplary embodiments, each group of eight cameras monitors a 60 inch lateral segment of the paper on the roller 30. Thus, the entire station 70 monitors a web having a total width of 120 inches. Moreover, the inspection station is modular in construction; additional sets of light modules and camera can be added to integrate the station into paper making machines having larger lateral widths.

Figure 5:
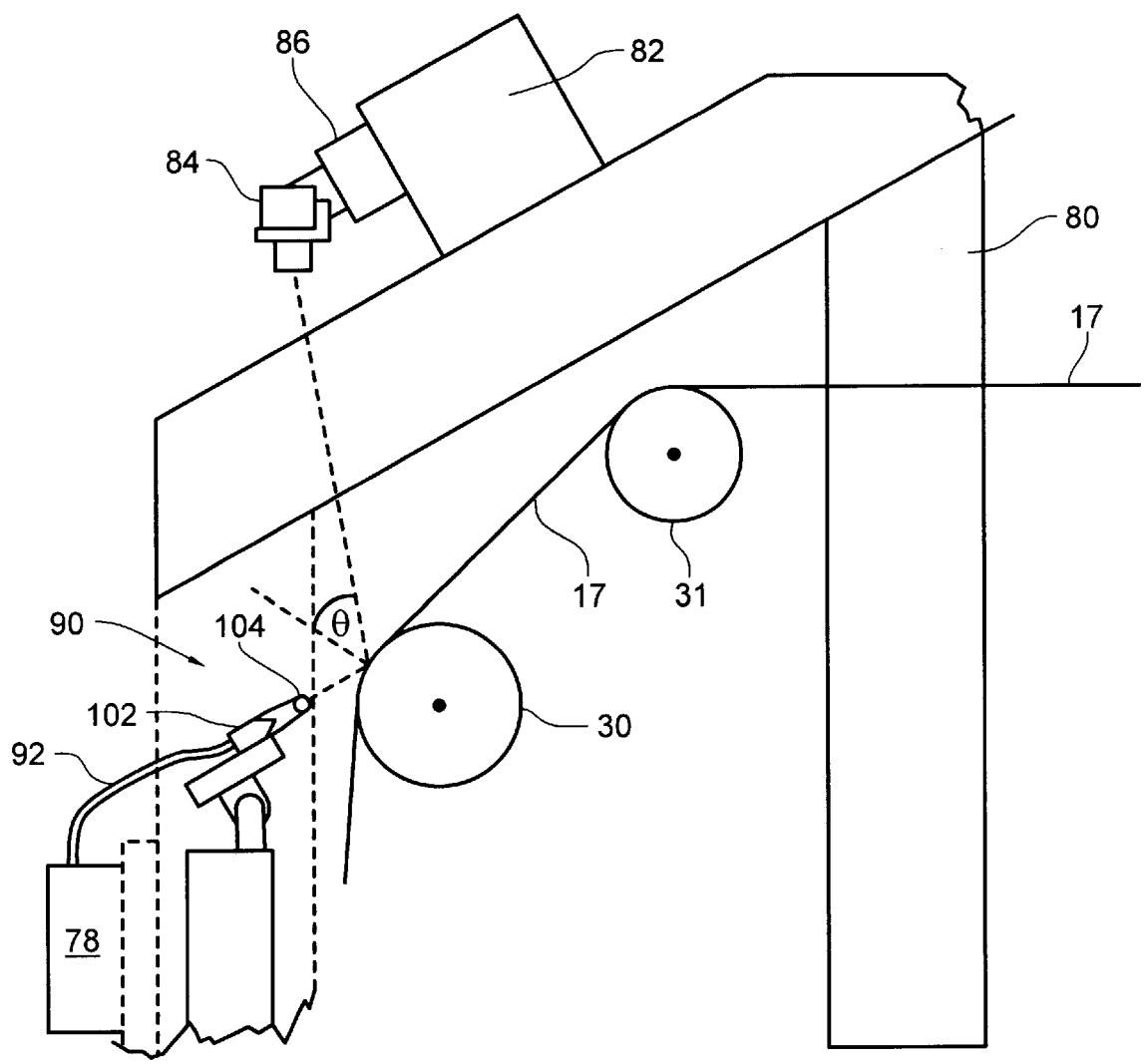
FIG. 5 shows another view of the paper inspection machine of FIG. 4.

FIG. 5 shows a cross-section of the optical inspection system shown in FIG. 4. In one exemplary embodiment, the light source 78 includes a 200 watt halogen bulb (although other light sources can be used). The white light generated thereby is fed via fiber optic cable 92 to a fiber optic head end 102, which laterally disperses the white light. The dispersed light is then focused by a rod lens 104 onto the paper 17 passing over the roller 30. The light is reflected from the paper 17 and received by camera 84, which includes a linear CCD array. The angle θ which the reflected light forms with respect to the normal of the roller 30 can be chosen to maximize detection of the bands. In one exemplary embodiment, the angle θ equals approximately 55 degrees. Signals from the CCD array are thereafter fed to a computer unit (e.g. units 72 or 76) for analysis.

Figure 6:
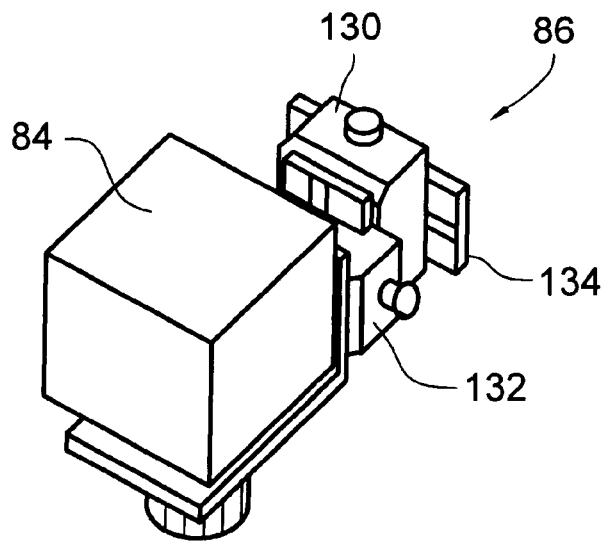
FIG. 6 shows an enlarged view of a camera employed in the paper inspection machine of FIG. 4.
Figure 7:
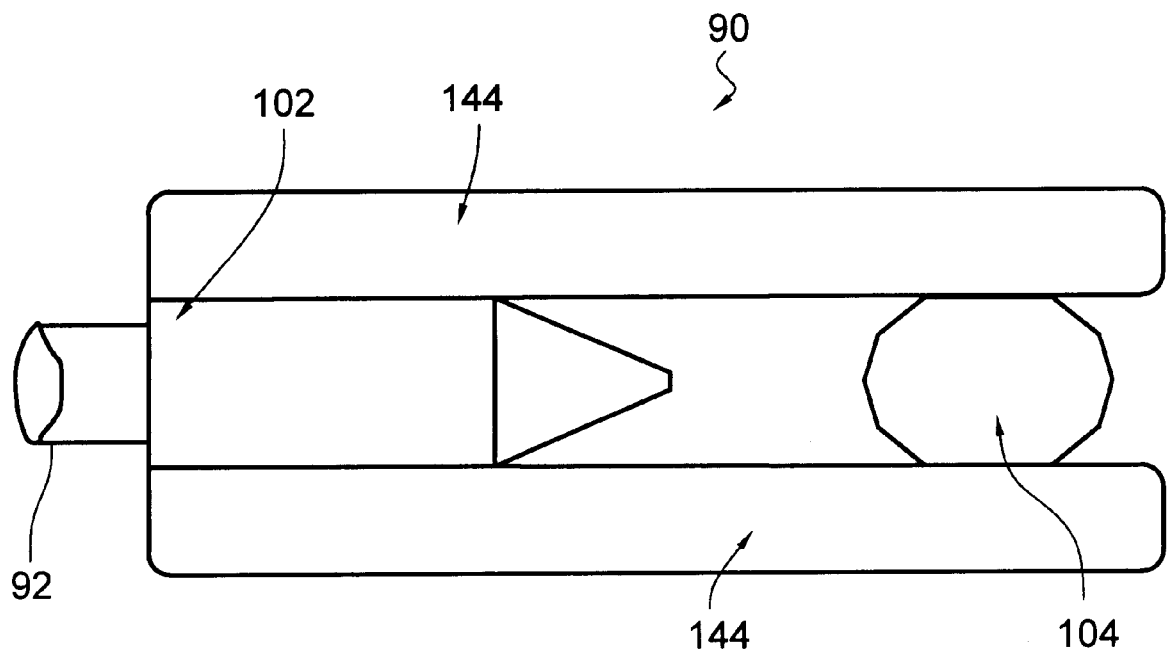
FIG. 7 shows an enlarged cross-sectional view of the light distribution assembly employed in the paper inspection machine of FIG. 4.

A still more detailed depiction of the camera assembly 84 and light distribution assembly 90 can be found in FIGS. 6 and 7, respectively. FIG. 7 shows a cross-section of the light distribution assembly 90. The assembly includes an optic head end 102, which laterally disperses the white light. The dispersed light is then focused by a rod lens 104 onto the paper 17 to form a narrow illuminated stripe across the paper. Head end 102 and rod lens 104 are sandwiched between two plates 144 which span the length of the roller. The light distribution assembly 90 is fed light via fiber optic cables (one of which is denoted by 92) from light sources (one of which is denoted by 78). By way of example, a rod lens assembly produced by Fostec can be used for the light distribution assembly 90.

As shown in FIG. 6, the camera includes a housing containing the linear CCD array. The housing is attached to the adjustment mechanism 86 which allows the operator to adjust both the azimuth and elevation of the camera via elements 130 and 132, respectively. The adjustment mechanism includes plate 134 which allows the camera assembly 84 to be attached to the overhead member 82 of the frame 80 (as illustrated in FIGS. 4 and 5). By way of example, a camera produced by EG&G Reticon can be used for the camera 84.

Figure 8A:
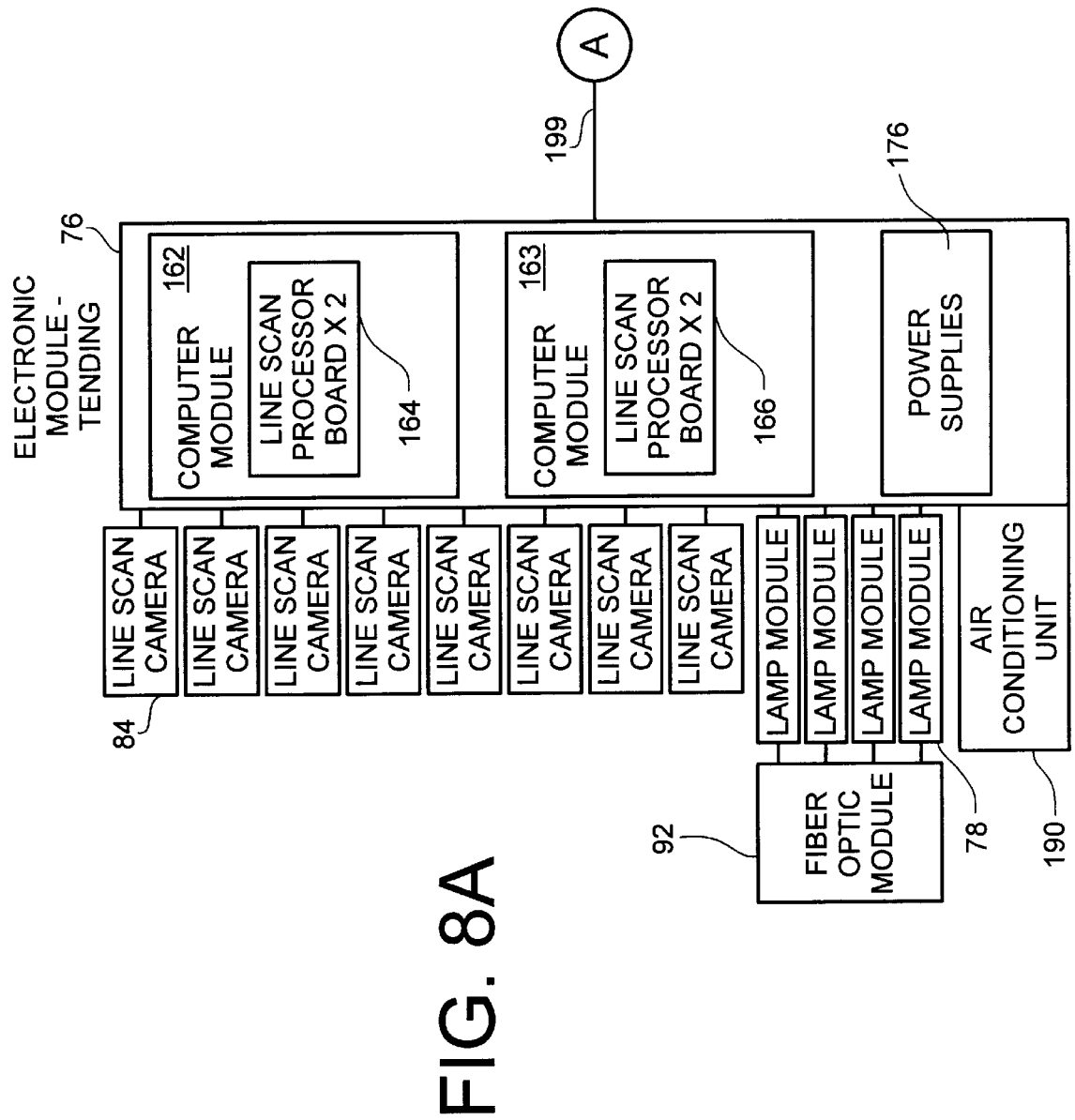
FIGS. 8A and 8B show an exemplary electrical system for use in conjunction with the paper inspection machine of FIG. 4.
Figure 8B:
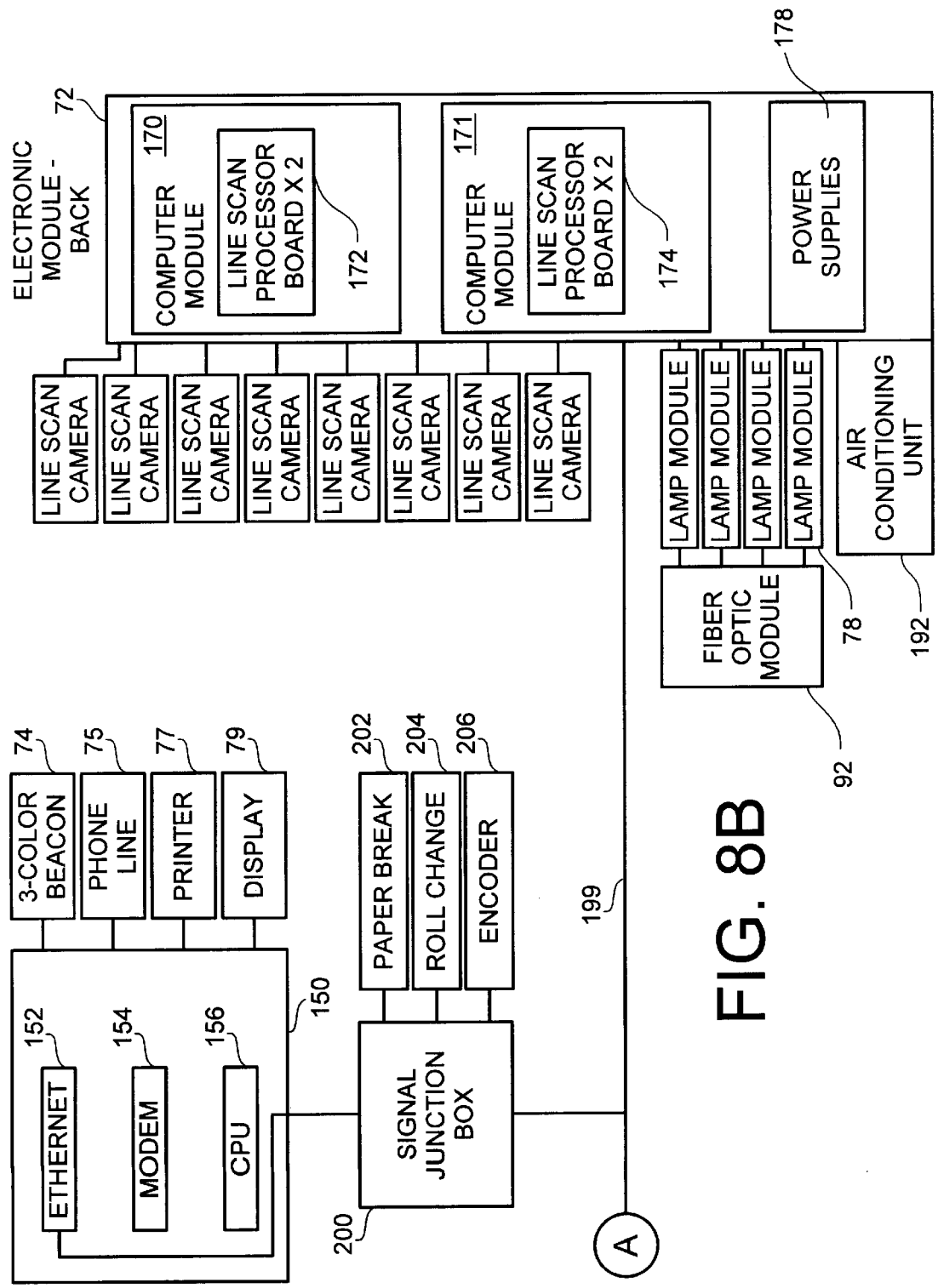

The electrical signals generated by the CCD arrays of the camera (such as 84) are fed to the processing circuitry enclosed by one of the units 76 or 72. More specifically, as shown in FIG. 8, the unit 76 includes two computer modules 162 and 163, preferably including Pentium™ processors (not shown). Each computer module includes plural line scan processor boards connected thereto for processing data received from the line scan cameras. In the embodiment shown in FIG. 8, computer module 162 has two processor boards 164 connected thereto and computer module 163 includes another two processor boards 166 connected thereto. Each processor board services two cameras. As will be discussed in further detail below, the units 76 and 72 determine the presence of bands and compute statistical information pertaining to the bands. This statistical information is transmitted at periodic intervals via an Ethernet interface (not shown) over line 199 to a signal junction box 200. The junction box, in turn, channels the data from the units 76 and 72 to a separate computer workstation 150 (not shown in FIGS. 3 or 4). Unit 72 has an identical construction to unit 76. Unit 72 includes two computer modules, 170 and 171. Computer module 170 has two line scan processor boards 172 connected thereto, and computer module 171 has another two processor boards 174 connected thereto.

As the lamps (e.g. 78) and other components of the station 70 can generate heat during their operation, the electronic units 76 and 72 include air conditioning units 190 and 192, respectively. Alternatively, the electronic units 76 and 72 can be cooled with conditioned air from a separate detached air conditioning system (not shown). An interconnected network of conduits (not shown) can also channel pressured air to the cameras (e.g. 84). The pressured air cools the cameras and also helps keep the cameras free of residue which otherwise would settle on the cameras and degrade their performance. Power sources 176 and 178 provide power to the various components of the system 70. The specific connection of electrical components will be readily apparent to those skilled in the art, and thus need not be discussed in detail.

In addition to data from the line scan camera, the junction box routes signals from a paper break sensor 202, new roll input 204, and an encoder 206 or tachometer (not shown in FIGS. 3 or 4). The paper break sensor 202 includes an infrared detector located adjacent to the moving web at some point along the wire 49 (with reference to FIG. 3). As the name suggests, this sensor provides an active high or low signal when the web is discontinued for some reason, such as a breakage. The new roll input 204 is a button which the user depresses to signal the start of a production run. This input can be used to inform the workstation 150 to begin accumulating statistics for a new production run. The button can be physically located on or near the workstation 150.

The encoder is a device which monitors the velocity of the moving web, and thereby provides a frame of reference by which the output of the camera can be correlated with the actual width of bands and band spacings. According to one exemplary embodiment, the encoder includes a collar which is mounted on a roller in the paper making machine, in conjunction with a nearby magnetic sensor. The collar includes magnetic inserts attached thereto. When the collar is rotated, the inserts come in close proximity to the sensor, upon which the sensor generates a pulse. The rate of pulses from the sensor is related to the rate of rotation of the roller, and in turn, the velocity of the web moving over the roller.

The workstation 150 includes a CPU 156, modem 154 and Ethernet interface 152. The output of the workstation can be channeled to a 3-color beacon 74 (to be described later), to a remote computer via phone line 75, a printer 77 and/or a display 79. The transfer of information via modem 154 to a remote computer allows a remote technician to perform diagnostic evaluation from a remote site. An InterColor™ industrial workstation can be used for the workstation 150.

Figure 9:
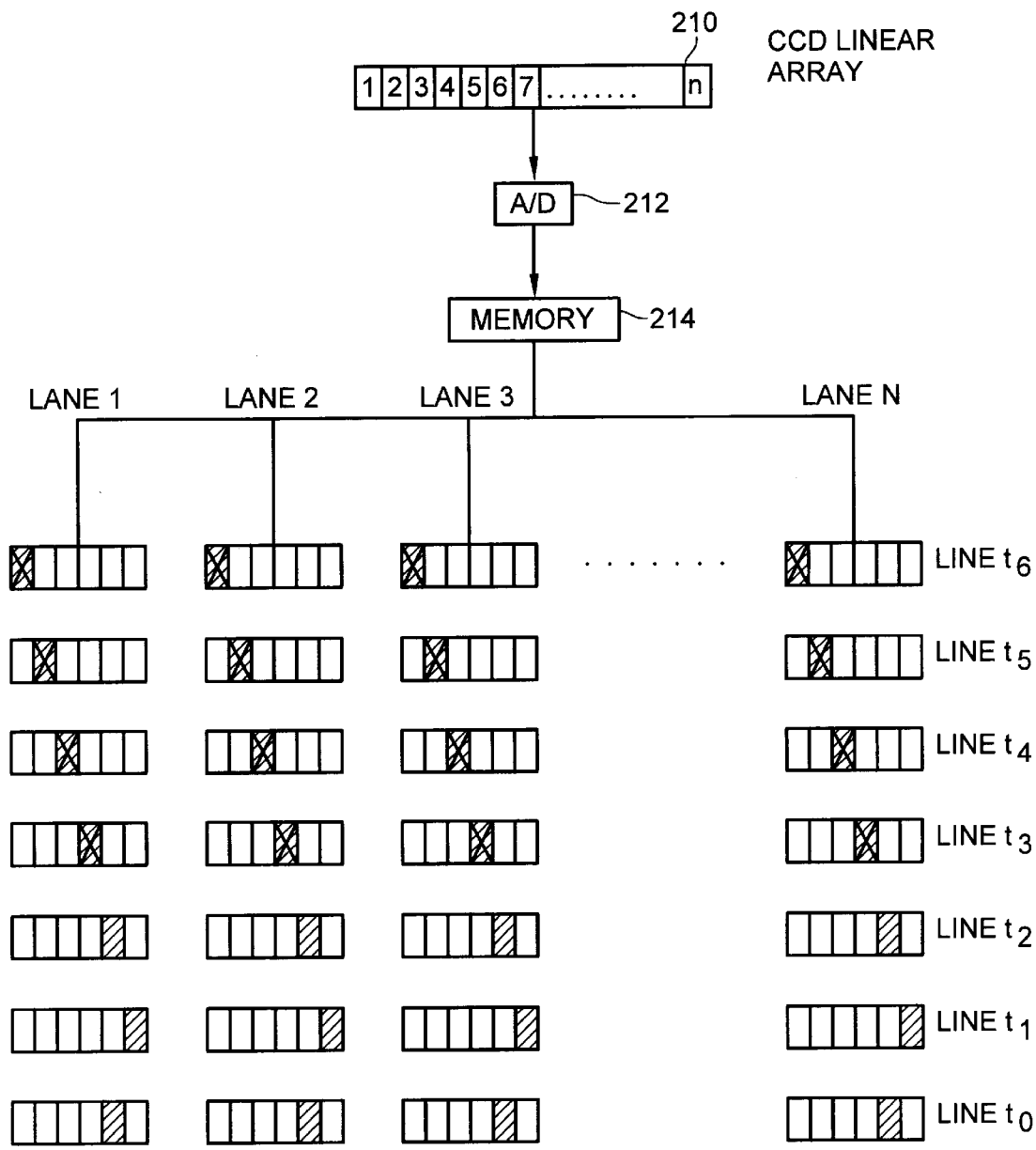
FIG. 9 shows an exemplary technique for processing data from a line scan camera.
Figure 10:
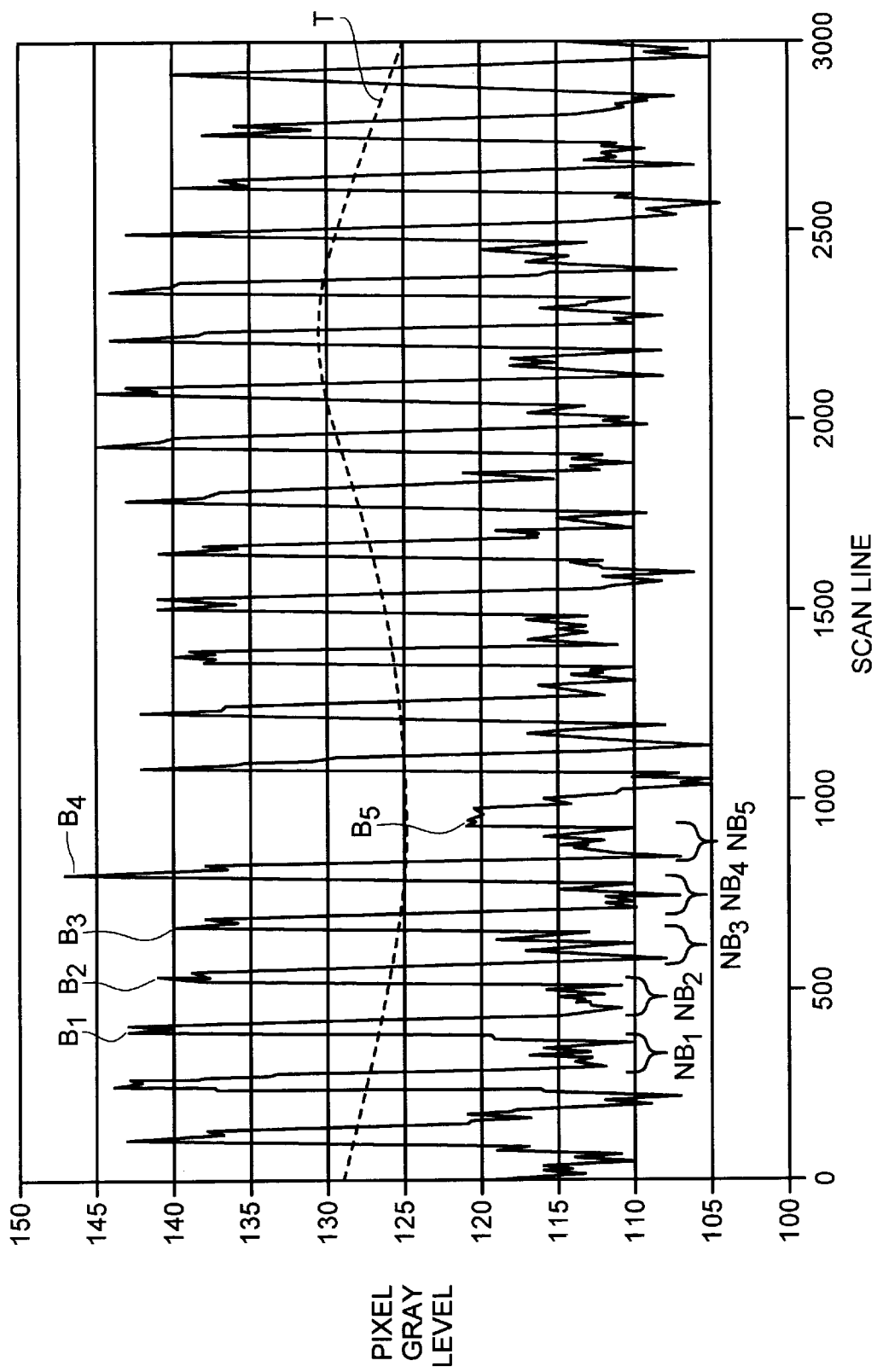
FIG. 10 shows an exemplary waveform of pixel gray level as a function of scan line.
Figure 11:
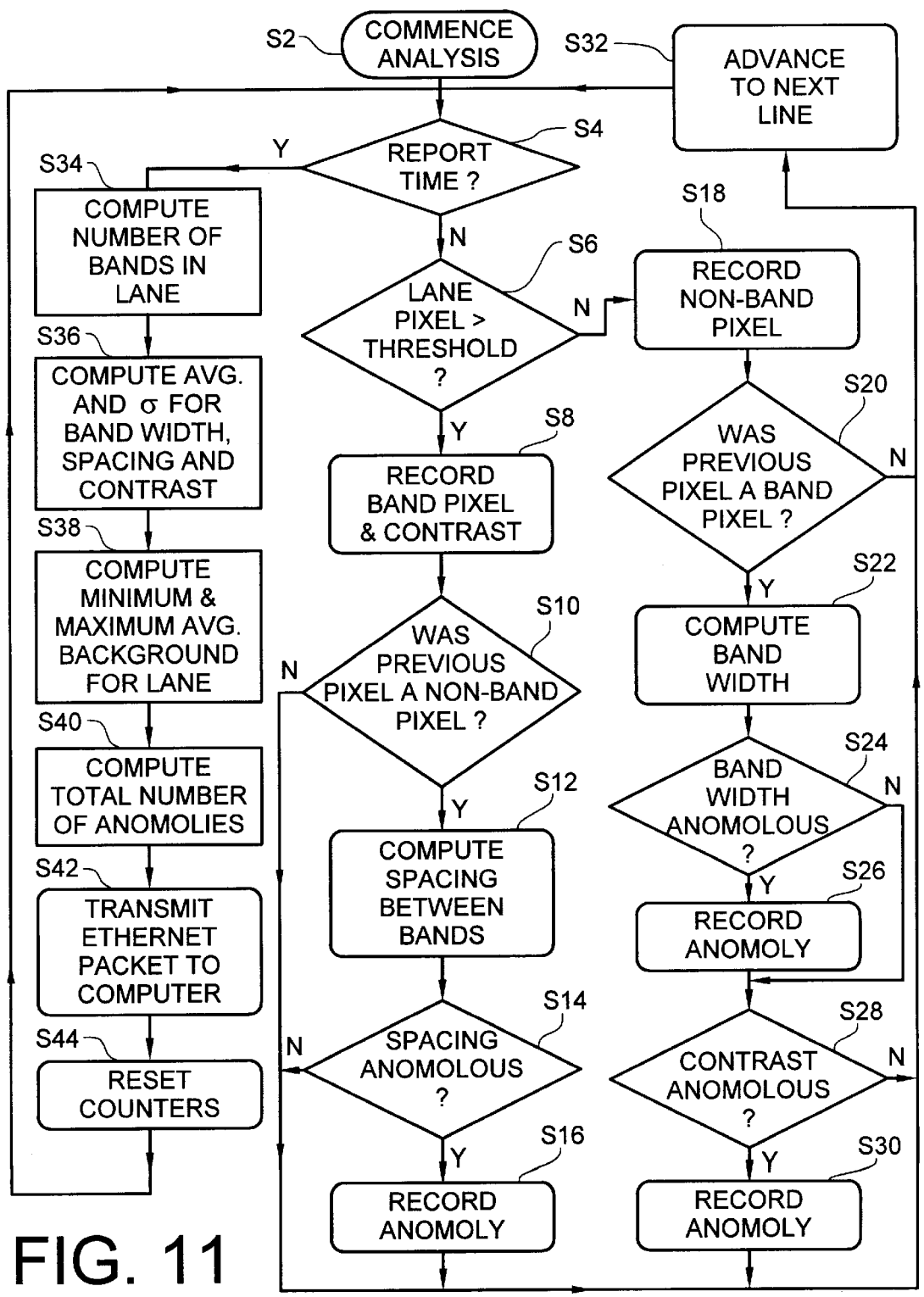
FIG. 11 shows an exemplary algorithm for determining various properties of the bands imaged by the line scan cameras.

The processing of the data from the line scan cameras by the processing units 76 and 72 can be understood by reference to FIGS. 9–11. As shown in FIG. 9, each camera (e.g. 84) includes a linear CCD array 210. For instance, the camera can employ a 1024×1 CCD array which spans a 7.5 inch portion of the web. The exemplary resolution of the array in the lateral direction across the roller 30 is 0.2 mm. Furthermore, the CCD array is exposed at a rate which allows the computer to sample information at a resolution of 0.2 mm in the longitudinal direction. Thus, the array effectively samples elements having a spatial dimension on the paper of 0.2 mm ×0.2 mm. Accordingly, each element of the CCD array includes a value indicative of the magnitude of the reflection sensed in a 0.2 mm×0.2 mm portion of the moving web.

The data from each linear array is thereafter converted from analog to digital form in A/D converter 212 and stored in memory 214 of one of the processing units 76 or 72. The processing unit then divides the data from each array into a series of contiguous lanes (e.g. a total of 32 lanes total in one embodiment). To facilitate discussion, each lane shown in FIG. 9 comprises 6 contiguous pixel elements, although each lane will typically include many more pixels. The magnitude of each pixel is quantified into one of, for example, 255 different levels.

During each exposure, a single pixel from each lane is compared with a dynamic threshold. Pixels above the given threshold are indicative of banded regions of the web, while pixels below the given threshold are marked as non-banded regions. Upon the next exposure, the next contiguous pixel in the lane is exposed, and the comparison is repeated. For example, at an arbitrary time denoted $t_0$, the fifth pixel in each lane is compared with the dynamic threshold (e.g. see bottom-most row of lanes denoted as "line $t_0$"). In the next exposure, the sixth element is compared to the threshold (e.g. see the rows of lanes denoted as "line $t_1$"). After this, the system will continue back in the opposite direction, choosing the fifth pixel for comparison with the threshold in line $t_2$. Thus, the pixel chosen for comparison with the threshold varies in a serpentine path, as generally denoted by FIG. 9.

According to another embodiment, the inspected pixel is not advanced at each line. Rather, in this embodiment, the processing unit can dwell on each pixel for a prescribed number of lines (e.g. corresponding to 30 mm), after which it will advance to a next adjacent pixel. The comparison of only one pixel from each lane enhances processing speed without significantly degrading performance.

The pixel elements marked with an "X" denote a pixel value above the threshold. Thus, it is seen that a band started at line $t_3$.

According to one exemplary embodiment, the threshold used to detect a band region and a non-band region varies to accommodate changes in the base paper, band material, or measuring environment. For instance, as shown in FIG. 10, an exemplary waveform of pixel gray level as a function of scan line shows local perturbations which represent transitions from background non-banded regions (e.g. as in regions $NB_1$, $NB_2$, $NB_3$, $NB_4$ and $NB_5$) to banded regions (e.g. as in regions $B_1$, $B_2$, $B_3$, $B_4$ and $B_5$). The waveform also shows a global change in which the general baseline of these local perturbations slowly undulates. For example, the global undulation is at its lowest point around the scan line 1000, and at its highest point around scan line 2000. This global undulation is primarily due to changes in the basis weight of paper caused by uneven application of pulp by the paper making machine. The present invention takes this phenomenon into account by adjusting the threshold level (T) so that it generally tracks the changing baseline of the waveform.

One technique for dynamically varying the threshold level is described as follows. Generally, the threshold at any given moment is a function of the gray levels of the immediately preceding band region or regions, and the gray levels of the immediately preceding non-band region or regions. In one embodiment, the threshold represents a moving average of previous non-band background (e.g. an average of $NB_1$, $NB_2$, etc.) plus the greater of (1) a set constant (such as 10 gray levels), or (2) 50% of the moving average of peak heights of the banded regions (e.g. an average of the heights of $B_1$, $B_2$, etc.). For example, consider the band region $B_3$. The threshold used to discriminate this band region is determined by first calculating the average background level of the non-band regions $NB_2$ and $NB_3$. Thereafter, an average peak height value is determined by computing the average of the heights of the $B_1$ and $B_2$ band regions. The "height" of a band region generally corresponds to the difference in pixel gray level between the band region and a subsequent non-band region. In making this measurement, a single gray level can be used to represent the gray level of the band region (such as the maximum gray level), or an average of gray levels within the band region can be used. Similarly, a single gray level can be used to represent the gray level of a subsequent non-banded region, or an average of gray levels within the subsequent non-banded region can be used. After computing the peak heights in this manner, half of the average peak heights (e.g. from $B_1$ and $B_2$) is compared with the preset value. The greater of the two is added to the average background level (computed above) to derive the threshold value. For example, the average of the heights of $B_1$ and $B_2$ is approximately 30 gray levels, half of which is 15 gray levels. If the preset value is set at 10 gray level values, then the algorithm will select 15 as the value to be added to the average background. However, if a series of shorter peaks (such as $B_5$) are encountered, then the algorithm will rely on the preset value (e.g. of 10 gray levels) to discriminate band regions from non-band regions. The preset value is preferably set at least high enough so that noise in the non-banded region will not be misinterpreted as the start of a band region.

It will be readily apparent to those skilled in the art that the window selected for calculating the moving average of peak heights and non-banded region levels need not be restricted to two banded regions and two non-banded regions, respectively. A smoother threshold can be obtained by widening the window. Furthermore, the above discussed threshold levels are dependent on the type of paper and the band material used, as well as the operating environment; the specific values cited above are entirely exemplary.

The actual task of determining the characteristics of the bands can be understood with reference to the flowchart shown in FIG. 11. The analysis commences at step S2, followed by a determination whether it is time to report data from the processing units 76 and 72 to the workstation 150 over the Ethernet network 199 (step S4). In an exemplary embodiment, the processing performed by units 76 and 72 is reported every half second. However, having just commenced analysis, the results of this query will be answered in the negative, and the system will advance to step S6. In step S6 it is ascertained whether the pixel in a lane is above the dynamic threshold. To facilitate discussion, step S6 is framed in the context of a single lane of a single linear array from a single camera.. However, it should be kept in mind that the system includes a plurality, e.g. 16, similarly constituted cameras each with their own linear arrays and the output of each array is divided into a plurality of lanes. Thus the comparison shown in step S6 is in actuality repeated many times for different lanes and different cameras. Preferably the processing units perform the computations for different cameras in parallel to improve processing speed.

If it is determined in step S6 that the magnitude of the pixel is above a dynamic threshold, then the algorithm advances to step S8, where the presence of a banded pixel and its contrast are recorded. If the previous pixel in the previous line was not a band pixel (as determined in step S10), then the current line represents a start of a band. This would correspond to line $t_3$ shown in FIG. 9, since the previous line at $t_2$ contained a pixel below the dynamic threshold. It is therefore possible at this time to determine whether the spacing between the present band and the last encountered band (if appropriate) is within prescribed tolerances (steps S12 and S14). If the band spacing is either too long or too short, this fact is logged in step S16, whereupon the algorithm advances to the next line in step S32.

If, on the other hand, the pixel examined in step S6 is below the dynamic threshold, then this fact is recorded in step S18. It is then determined if the previously examined pixel in the previous line was a band pixel (step S20). If so, this marks the end of a band, and it is possible to determine the average contrast of the band and the width of the band (step S22). It is determined whether these values are outside of prescribed tolerances (steps S24–S30). If so, these anomalies are recorded and the algorithm advances to the next line in step S32.

Supposing, at this time, it is determined that a half of a second has elapsed (in step S4). This causes the processor units 76 and 72 to enter their report mode. As shown in FIG. 11, the units will compute the number of bands in the lane over the last half of a second (step S34), the average and standard deviation for band width, band spacing and band contrast (step S36), the minimum and maximum average background for the lane (step S40) and the total number of anomalies (e.g. out-of-tolerance band width, spacing and contrast) (step S40). This information is assembled into a packet which is forwarded to the workstation 150 (step S42), and then the various counters are reset (in step S44).

Figure 12A:
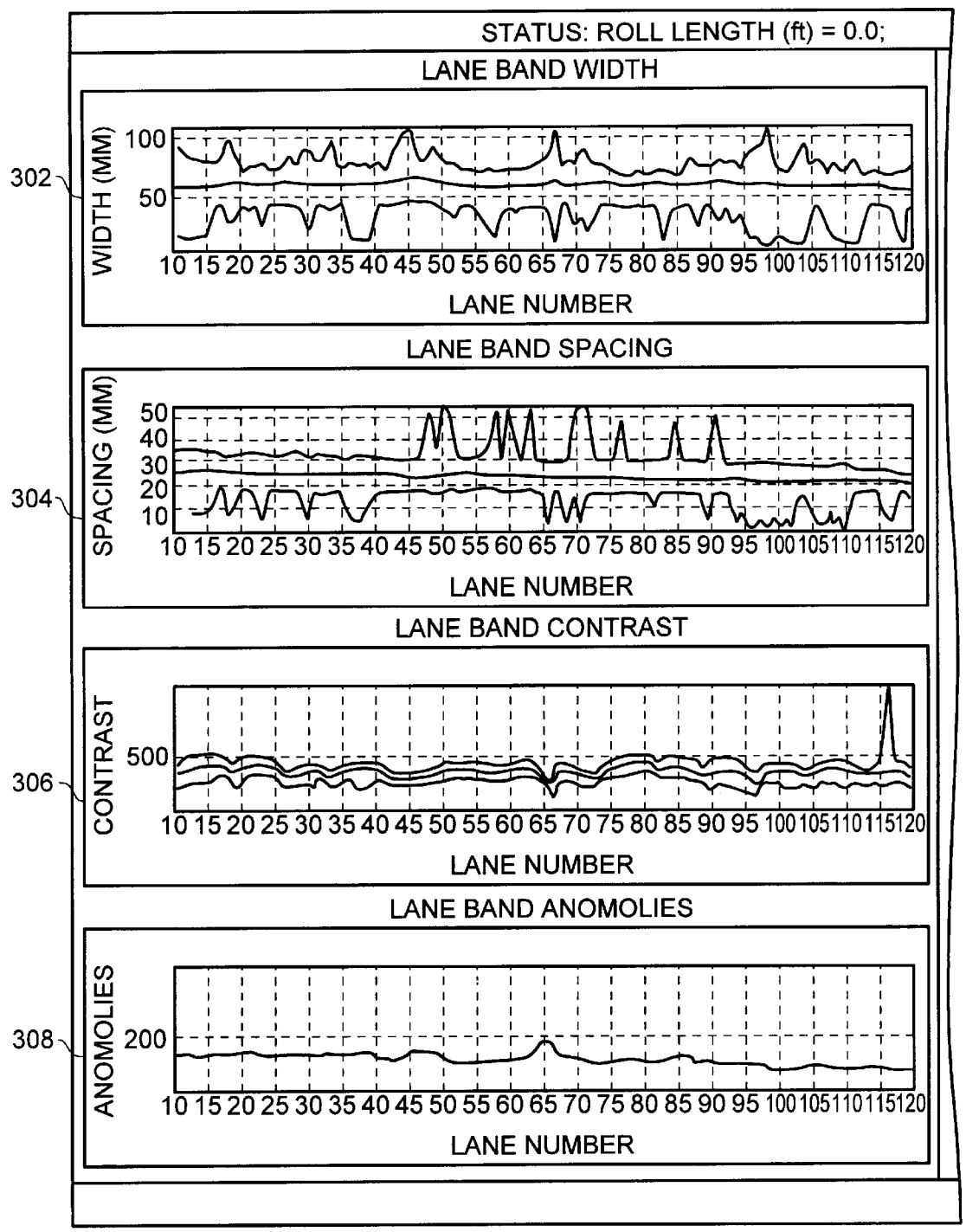
FIGS. 12A and 12B show an exemplary graphical display of various properties of the bands imaged by the line scan cameras.
Figure 12B:
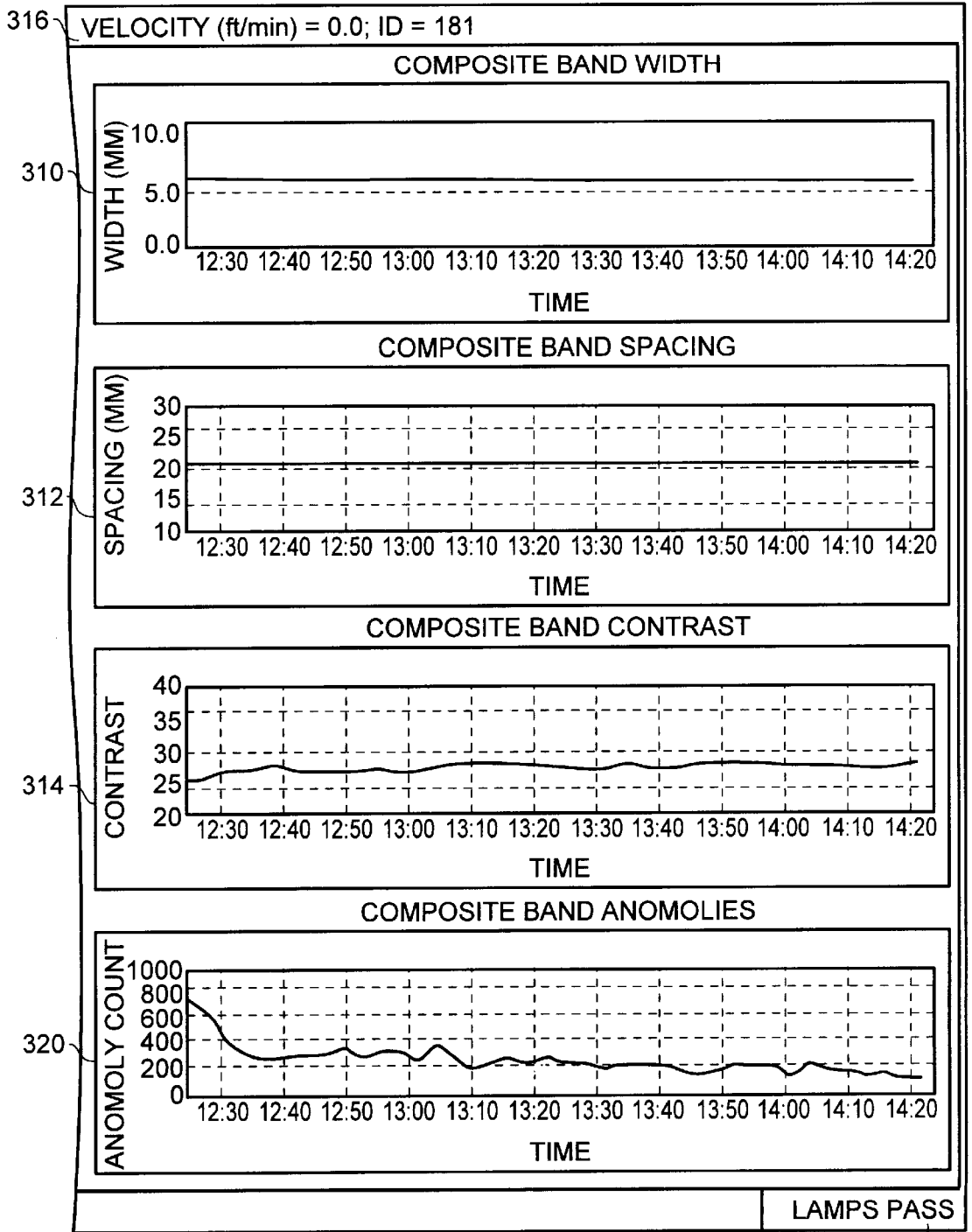

The workstation then aggregates this information with previously transmitted information to provide a statistical summary of the operation of the band application assembly 99 (of FIG. 3). This information is displayed on display panel 300 as illustrated in FIGS. 12A and 12B. The panel 300 includes a first subpanel 302 listing the band width as a function of lane number for the last reporting interval. A subpanel 304 illustrates band spacing as a function of lane number for the last reporting interval. A subpanel 306 illustrates band contrast as a function of lane number for the last reporting interval. Finally, subpanel 308 illustrates the number of band anomalies (aggregate of band spacing, band width, and contrast anomalies) as a function of lane number for the last reporting interval. The subpanels 302, 304 and 306 contain a middle line indicating the average values of the band width, band spacing and band contrast over the half second interval of reporting. The two other curves bracketing the middle curves denote the plus and minus $3\sigma$ readings. The middle curve can be shown in green, while the $3\sigma$ curves are shown in red so that they can be more readily distinguished.

In addition to the current lane summary, the workstation 150 provides statistics summarizing the performance of the band application assembly 99 since the start of operation. Notably, subpanel 310 illustrates the composite band width (e.g. the average bandwidth) as a function of time. Subpanel 312 illustrates composite band spacing 312 as a function of time. Subpanel 314 shows composite band contrast as a function of time. And finally, subpanel 320 shows the number of band anomalies as a function of time. Thus, with the right-hand subpanels, it is possible to observe any trends in degradation. With the left-hand subpanels, it is possible to observe specific points in the lateral span of the web which are producing out-of-tolerance bands, band-spacing or band contrasts, which can be caused by clogged pulp applicators.

In addition to these graphs, the workstation 150 presents status information 316 regarding the roll length, the velocity of the web (from the encoder or a tachometer) and a sample id (which the user enters in advance to label the run). All of the above data can be stored for further non-real-time analysis. The run is indexed by the ID number.

The interface software of the workstation 150 additionally includes routines to monitor system parameters to determine system status. When an anomaly is detected, the operator interface will display a message identifying the most-likely cause of the anomaly. In the panel 317 shown in FIGS. 12A and 12B, the message indicates that lamps are currently functional. The software also controls a 3-color beacon that can be mounted at any of various locations, such as on the workstation 150. The beacon flashes red to denote a system failure, yellow to denote an inspection inhibited mode, and green to denote an inspection active mode.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention as defined by the following claims.

By way of example, the present invention has been described in the context of detecting bands located on cigarette paper. But the present invention extends to the detection of any information formed on sheet-like material. For instance, the present invention can be used to detect bands on other papers, including papers prepared for security purposes, such as paper currency, stock certificates, bearer negotiable bonds, etc.

What is claimed is:

1. An inspection station for inspecting a web containing bands, comprising;

a source for generating electromagnetic radiation;

a conduit for directing said electromagnetic radiation from said source;

a distribution assembly for receiving the electromagnetic radiation directed from said source by said conduit, and directing said electromagnetic radiation onto a web of material to induce reflections from a surface of said web;

a line scan camera for receiving said reflections, and generating output signals; and a processing unit for processing said output signals, said processing unit ascertaining the characteristics of said bands from said output signals.

2. The inspection station of claim 1, wherein the distribution assembly includes an elongate rod lens for directing said light onto said web.

3. The inspection station of claim 1, wherein the line scan camera includes a linear CCD array.

4. The inspection station of claim 1, including at least one other source connected to said distribution assembly by another conduit, and including at least one other camera for receiving said reflections.

5. The inspection station of claim 1, wherein said bands comprise plural banded regions amongst plural non-banded regions.

6. The inspection station of claim 5, wherein said processing unit ascertains one or more of the follow web properties:

the spacing between adjacent banded regions on said web;

the width of banded regions; and the contrast of banded regions.

7. The inspection station of claim 6, wherein said processing unit ascertains said one or more properties by dividing said output signals of said line scan camera into a plurality of lanes, and examines output signals within each output lane to determine whether the output signals are above or below a threshold, wherein output signals above said dynamic threshold are indicative of said banded regions, and output signals below said dynamic threshold are indicative of said non-banded regions.

8. The inspection station of claim 7, wherein said processing unit examines only one output signal in each lane.

9. The inspection station of claim 6, wherein said processing unit periodically transfers said ascertained one or more properties to a computer workstation, which accumulates said one or more properties with previously transferred properties to generate statistical displays.

10. The inspection station of claim 7, wherein said processing unit periodically transfers said ascertained one or more properties to a computer workstation, which accumulates said one or more properties with previously transferred properties to generate statistical displays.

11. The inspection station of claim 5, wherein said processing unit discriminates said non-banded regions from said banded regions using a dynamic threshold.

12. The inspection station of claim 11, wherein said dynamic threshold is computed as a function of a moving average of gray level values within one or more non-banded regions, and a moving average of relative gray level values within one or more banded regions.

13. A system for optically detecting the characteristics of paper containing banded regions and non-banded regions, comprising:

an inspection station including a light source for projecting a stripe of light laterally across a web to generate reflected radiation indicative of said characteristics, and a camera for receiving said reflected radiation to generate output signals;

at least one processing unit for processing said output signals generated by said camera to detect said characteristics, and for periodically transferring said detected characteristics to a computer workstation; and said computer workstation including statistical computing means for reporting said characteristics.

14. The system according to claim 13, wherein said at least one processing unit determines one or more of the following characteristics:

the width of said banded regions;

the spacing between said banded regions; and the contrast of said banded regions.

15. The system according to claim 14, wherein said processing unit determines said one or more characteristics by dividing the output signals from said camera into a plurality of lanes.

16. The system according to claim 15, wherein said workstation reports said one or more characteristics as a function of said plurality of lanes.

17. The system according to claim 14, wherein said workstation reports said one or more characteristics as a function of time.

18. The system according to claim 14, wherein said workstation reports identified ones of said one or more characteristics which do not meet prescribed tolerances.

19. A system for the manufacture of cigarette paper including banded regions and non-banded regions, including:

a slurry supply for the delivery of slurry to a head end, which forms a web of said slurry material;

a band applicator located downstream of said head end for forming one or more banded regions on said web; and an inspection station located downstream of said band applicator for determining the characteristics of said banded region and said non-banded regions, and the spatial relationship between said banded regions and said non-banded regions, said inspection station including a light source, a camera and a processing unit wherein light from said light source forms reflections on a surface of said web, said camera receives said reflections to generate output signals, and said output signals are processed in said processing unit.

20. A method for inspecting paper containing banded regions and non-banded regions, including the steps of:

directing light from a light source laterally across a web of said paper, said light forming reflections when it impinges on a surface of said web;

receiving said reflections by a camera to generate output signals;

processing said output signals in a processing unit to generate one or more of the following properties:
width of one or more banded regions;
spacing between one or more adjacent sets of banded regions;
contrast of one or more banded regions;
periodically communicating said one or more properties to a computer workstation; and
generating, at said computer workstation, statistical reports on the basis of said one or more properties communicated in said step of communicating.

21. The method for inspecting of claim 20, wherein said processing step performs a preliminary step of discriminating said non-banded regions from said banded regions using a dynamic threshold.

22. The inspection station of claim 21, wherein said dynamic threshold is computed as a function of a moving average of gray level values within one or more non-banded regions, and a moving average of relative gray level values withon one or more banded regions.

* * * * *